United States Patent [19]

Schaefer et al.

[11] Patent Number: 5,356,860
[45] Date of Patent: Oct. 18, 1994

[54] STYRENE DERIVATIVES USEFUL AS HERBICIDES AND DEFOLIANTS

[75] Inventors: Bernd Schaefer, Dierbach; Lothar Rueb, Speyer; Peter Schaefer, Bad Duerkheim; Karl-Otto Westphalen, Speyer; Matthias Gerber, Mutterstadt; Helmut Walter, Obrigheim, all of Fed. Rep. of Germany

[73] Assignee: BASF Aktiengesellschaft, Ludwigshafen, Fed. Rep. of Germany

[21] Appl. No.: 61,535

[22] Filed: May 14, 1993

Related U.S. Application Data

[63] Continuation of Ser. No. 813,635, Dec. 26, 1991, abandoned.

[30] Foreign Application Priority Data

Dec. 29, 1990 [DE] Fed. Rep. of Germany ....... 4042194

[51] Int. Cl.$^5$ ................ C07D 209/48; C07D 207/24; C07D 237/26; C07D 513/14; A01N 37/32; A01N 43/38
[52] U.S. Cl. .................. 504/165; 504/281; 504/283; 504/286; 504/236; 504/166; 504/169; 504/167; 544/235; 544/236; 544/237; 658/477; 658/478; 658/479; 658/471; 658/472; 658/473; 658/545; 658/546; 658/548; 658/362.5
[58] Field of Search ............. 548/471, 472, 473, 545, 548/546, 548, 477, 478, 479, 362.5; 544/235, 236, 237; 504/236, 281, 283, 286, 166, 167, 169, 168

[56] References Cited

U.S. PATENT DOCUMENTS

| | | | |
|---|---|---|---|
| 4,258,182 | 3/1981 | Beecken | 548/546 X |
| 4,914,190 | 4/1990 | Liechti et al. | 548/545 X |
| 4,933,001 | 6/1990 | Plath et al. | 71/96 |
| 4,958,043 | 9/1990 | Weaver et al. | 548/546 X |
| 4,997,472 | 3/1991 | Rueb et al. | 71/92 |
| 5,034,388 | 7/1991 | Clough et al. | 544/235 X |
| 5,062,884 | 11/1991 | Plath et al. | 71/95 |

FOREIGN PATENT DOCUMENTS

| | | | |
|---|---|---|---|
| 0410265 | 1/1991 | European Pat. Off. | 544/235 |
| 3714373 | 11/1988 | Fed. Rep. of Germany | 71/95 |
| 60-194189 | 10/1985 | Japan | 548/546 |

OTHER PUBLICATIONS

JP-A Kokai 27962/1986 Abstract Only.
Mali et al, Synthesis, vol. 10, pp. 862 to 865 (1984).
Matsumoto et al, Chemical Abstracts, vol. 105, #60524v (1986).
Plath et al, Chemical Abstracts, vol. 111, #77843v (1989).
Rueb et al, II, Chemical Abstracts, vol. 113, #'s 231369v, 231370p (1990).

*Primary Examiner*—Floyd D. Higel
*Attorney, Agent, or Firm*—Keil & Weinkauf

[57] ABSTRACT

Abstract of the Disclosure: Styrene derivatives I

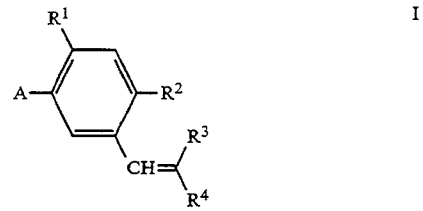

where $R^1$ is H or halogen, $R^2$ is halogen, $R^3$ is H, halogen or $C_1$-$C_4$-alkyl, $R^4$ is CN or $C_1$-$C_6$-alkylcarbonyl and A is a heterocyclic radical $A_1$ to $A_5$:

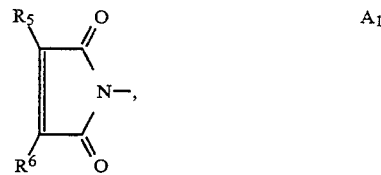

(Abstract continued on next page.)

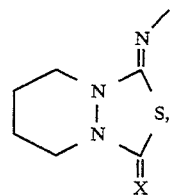
A4
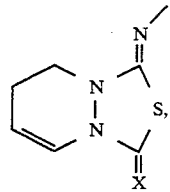
A5
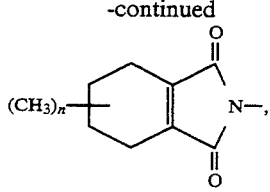
A2
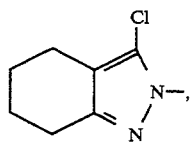
A3
where $R^5$ and $R^6$ are H, $CH_3$ or $C_2H_5$, n is 0 or 1 and X is oxygen or sulfur, with the proviso that $R^4$ is alkylcarbonyl when $R^1$ is H and at the same time A is $A_2$ where n is 0, and agriculturally useful salts thereof, processes for the preparation of the styrene derivatives I and herbicides containing them.
4 Claims, No Drawings

STYRENE DERIVATIVES USEFUL AS HERBICIDES AND DEFOLIANTS

This application is a continuation of application Ser. No. 07/813,635, filed on Dec. 26, 1991, now abandoned.

The present invention relates to novel styrene derivatives of the general formula I

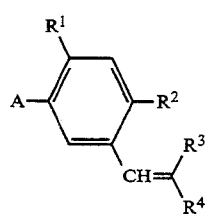

where $R^1$ is hydrogen or halogen, $R^2$ is halogen, $R^3$ is hydrogen, halogen or $C_1$–$C_4$-alkyl, $R^4$ is cyano or $C_1$–$C_6$-alkylcarbonyl and A is a heterocyclic radical selected from the groups $A_1$ to $A_5$

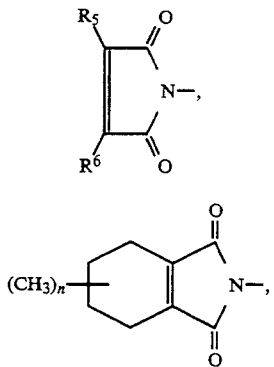    $A_1$

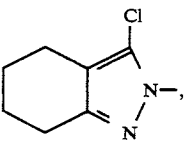    $A_2$

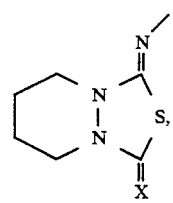    $A_3$

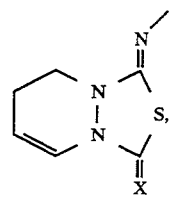    $A_4$ $A_5$ where $R^5$ and $R^6$ are each hydrogen, methyl or ethyl, n is 0 or 1 and X is oxygen or sulfur, with the proviso that $R^4$ is $C_1$–$C_6$-alkylcarbonyl when $R^1$ is hydrogen and at the same time A is the radical $A_2$ where n is 0, and agriculturally useful salts thereof, the formula I covering all isomeric forms of these compounds.

The present invention furthermore relates to processes for the preparation of these compounds and to herbicides and methods for the defoliation (desiccation) of cotton.

Japanese Preliminary Published Application JP-A Kokai 27962/1986, DE-A 37 24 399 and DE-A 39 17 767 disclose cinnamic esters of the structure I'

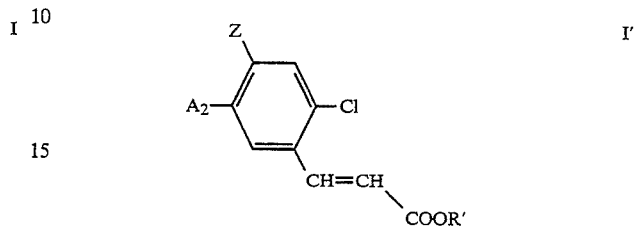

where Z is H or halogen.

Cinnamides and thioesters of the structure II'

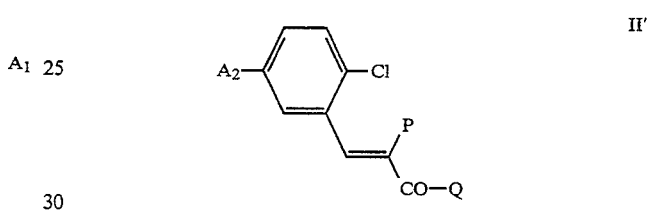

where P is halogen or alkyl and Q is amino or SR' form the subject of DE-A 39 01 705.

N-Phenyltetrahydroindazole derivatives ($A=A_3$) having a phenyl ether structure are disclosed in DE-A 39 01 550.

Since the compounds of the abovementioned prior art either do not have sufficient selectivity or are unsatisfactory with respect to the required application rates, it was an object of the present invention to provide compounds which have particularly good herbicidal activity. The compounds should also be capable of being used as bioregulators, in particular for the defoliation of cotton.

We have found that this object is achieved and that the styrene derivatives I defined at the outset have good herbicidal activity even at low application rates and are very suitable for the defoliation of cotton.

The compounds of the formula I are obtained by reacting a suitably substituted benzaldehyde of the formula II with a phosphorane of the formula III in a conventional manner, for example under conditions similar to those described in Synthesis 10 (1984), 862, in a solvent at from 0° C. to the boiling point of the solvent.

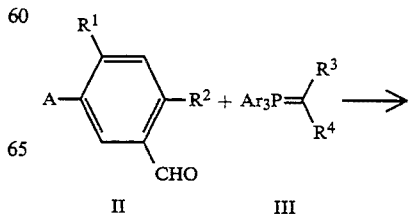

-continued

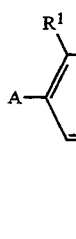

In formula III, Ar is unsubstituted or substituted aryl, phenyl generally being preferred.

The phosphoranes III which are required for the preparation of the styrene derivatives I and which are also referred to as phosphorylides are obtainable by methods known from the literature (e.g. Houben-Weyl, Methoden der Organisthen Chemie, Vol. E1, pages 636–639, Georg-Thieme Verlag, Stuttgart 1982 or Chem. Bet. 95 (1962), 3993).

The groups Ar of these phosphoranes may be unsubstituted or substituted phenyl radicals. The number of substituents per phenyl radical and the substitution pattern of the phenyl radicals are as a rule not critical for the success of the process, but a phenyl radical generally carries not more than 3 substituents. Preferred substituents of the phenyl radicals are those which are inert under the conditions of the process, for example the halides fluorine, chlorine or bromine, alkyl, preferably $C_1$–$C_4$-alkyl, in particular methyl, or $C_1$–$C_4$-alkoxy, in particular methoxy. As a rule, however, triarylphosphoranes III having an unsubstituted phenyl radical are preferred.

The reaction of starting compounds II and III is generally advantageously carried out in the presence of a solvent. Suitable solvents are all solvents conventionally used for carrying out the Witrig reactions, for example halogenated solvents, such as chloroform, or ethers, such as tetrahydrofuran, dioxane or ethylene glycol dimethyl ether. Preferred solvents are alcohols, in particular $C_1$–$C_4$-alcohols, such as methanol, ethanol, propanol, isopropanol, butanol, isobutanol or tert-butanol. The solvents may also be used in the form of solvent mixtures, but as a rule the pure solvents are preferably used.

In general, the reaction is carried out at from 0° to 100° C. The optimum reaction temperature is of course, however, dependent on the particular starting compounds II and III to be reacted and on the solvent used.

The starting compounds II and III can be reacted with one another in stoichiometric amounts. However, it may prove advantageous if one of the two reactants, II or III, is used in the reaction in an excess of from 0.05 to 5 times the molar amount.

The course of the Witrig reaction can be monitored by a conventional analytical method, such as thin layer chromatography or high pressure liquid chromatography. After the end of the reaction, the product I can be isolated by a conventional method, such as filtration or centrifuging, or by the addition of water followed by extraction. If required, the styrene derivatives I thus obtained can be further purified, for example by recrystallization or by a chromatographic method.

The above process generally gives the styrene derivatives I as cis/trans isomer mixtures with respect to the alkenyl side chain, as a rule the trans isomer predominating.

The process for the preparation of the styrene derivatives of the formula I also makes it possible to interchange the order in the synthesis of the benzaldehydes of the general formula II and the Wittig olefination.

In particular, it is possible to react suitable intermediates of the benzaldehydes II with the phosphoranes III before introducing the corresponding substituents in the benzaldehyde moiety to give the structure of the general formula I (as described further below for the example of the conversion of XVII to Ic).

The benzaldehydes of the general formula II which are used as starting materials are obtainable in a simple manner by the methods of DE-A 38 15 042 (=EP-A 340 708) or can be prepared, for example, as described below.

The benzo derivatives of the formula IIc are obtained according to the following reaction scheme:

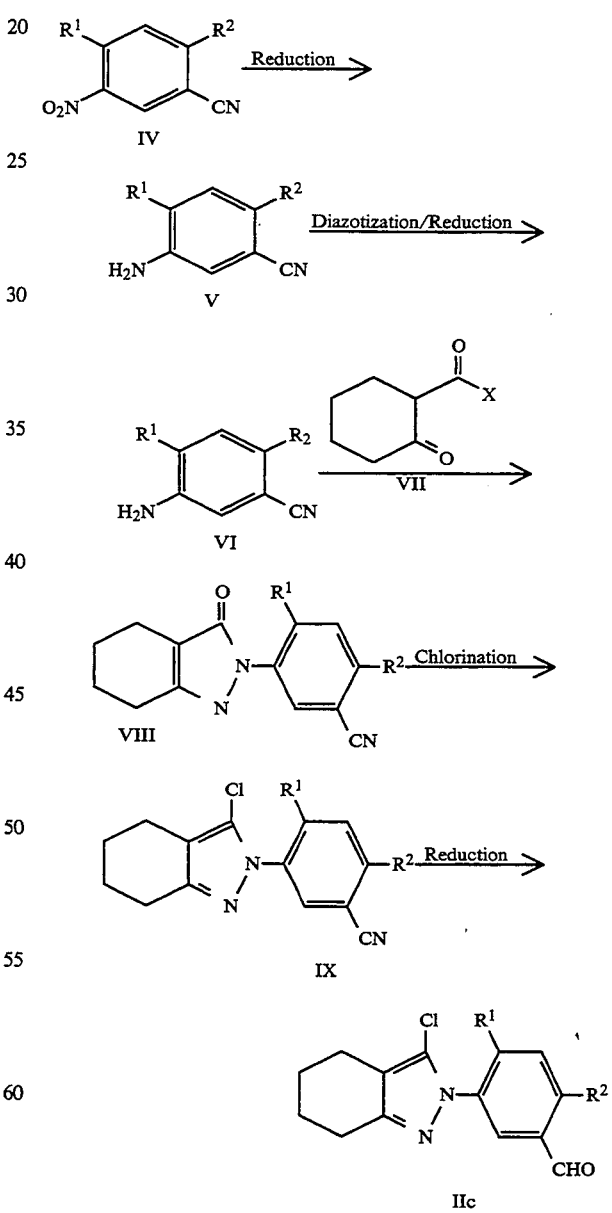

The reactions of IV to give the nitriles IX take place under the conditions described further below, similarly to the nitrostyrene derivatives XVIII.

The reduction of the nitriles IX to give the benzaldehydes is carried out by methods similar to those known from the literature (e.g. C. Ferri, Reaktionen der organischen Synthese, Georg Thieme Verlag, Stuttgart 1978, page 100).

The benzaldehydes of the formula IId, e are obtained if an aniline derivative of the formula X is first converted with thiophosgene, under the conditions described for XIX, into the corresponding isothiocyanate XI, the latter is subjected to an addition reaction with a piperazine XII and the resulting thiourea derivative XIII is cyclized with acidic cleavage of the acetal group with a phosgenating agent to give the aldehyde function or to give the aldehyde IId, e.

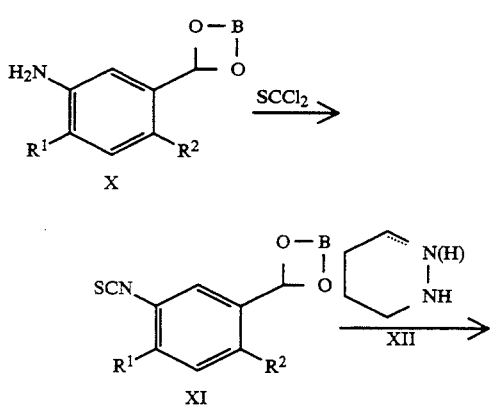

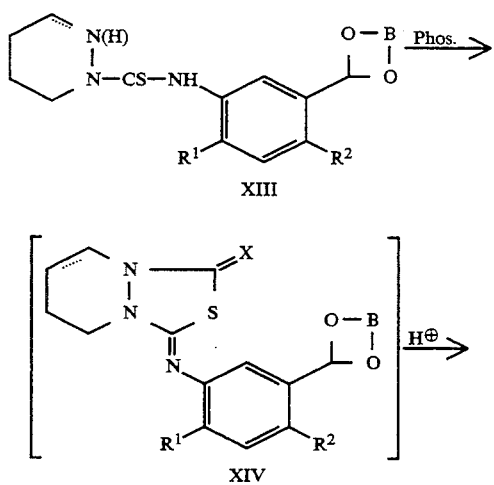

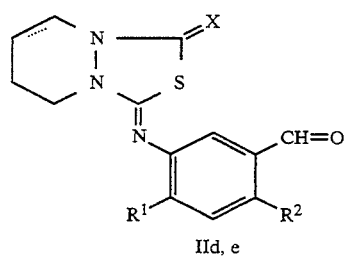

In formulae X, XI, XIII and XIV, B is an ethylene or propylene unit which may carry from one to three alkyl groups, such as methyl, ethyl, propyl or 1-methylethyl, preferably methyl. The dotted line in formulae XII, XIII, XIV and IId, e is a $\pi$ bond which may be present.

The reactions of X to give XI, of XI to give XIII and of XIII to give XIV take place under the conditions described below, similarly to the second synthesis variant of Id, e.

The acetal group in compound XIV is converted into the aldehyde function under acidic conditions, for example in the presence of a mineral acid, such as hydrochloric acid or sulfuric acid, or an organic acid, such as p-toluenesulfonic acid.

The compounds I having the radicals $A_1$ and $A_2$ are also obtained, for example, by condensing an aniline of the general formula XV with an anhydride of the general formula XVI a or b.

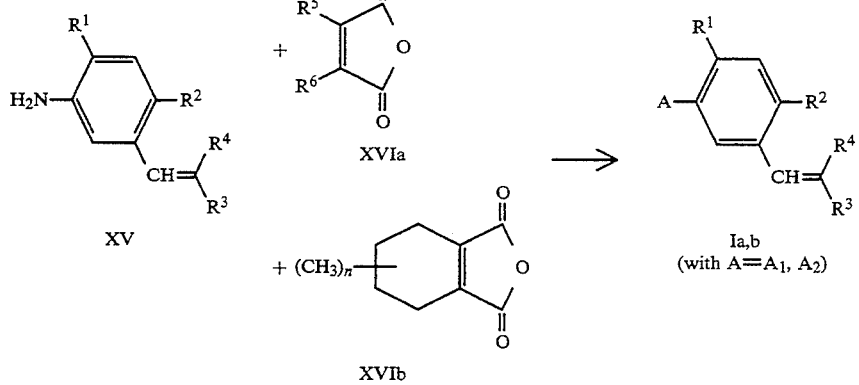

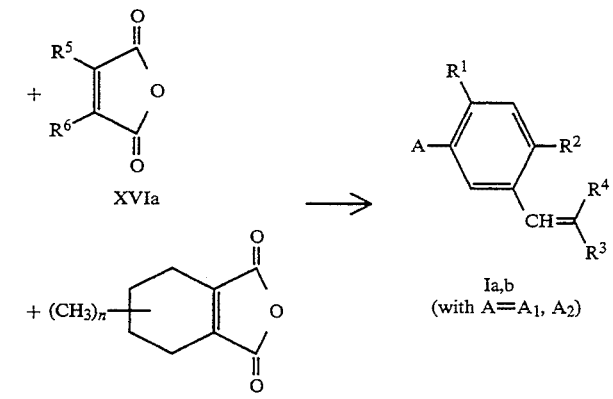

Inert organic solvents, such as lower alkanoic acids, e.g. acetic acid, propionic acid or isobutyric acid, and the esters of these acids, such as ethyl acetate, relatively high boiling hydrocarbons, such as toluene and xylene, and/or dimethylformamide, are used for the condensation. The reaction is carried out as a rule at from 25° C. to the boiling point of the particular reaction mixture, preferably at from 50° to 140° C. When an aprotic solvent is used, it is advisable to remove the water continuously.

The compounds Ic having the radical $A_3$ are also obtained according to the reaction scheme below.

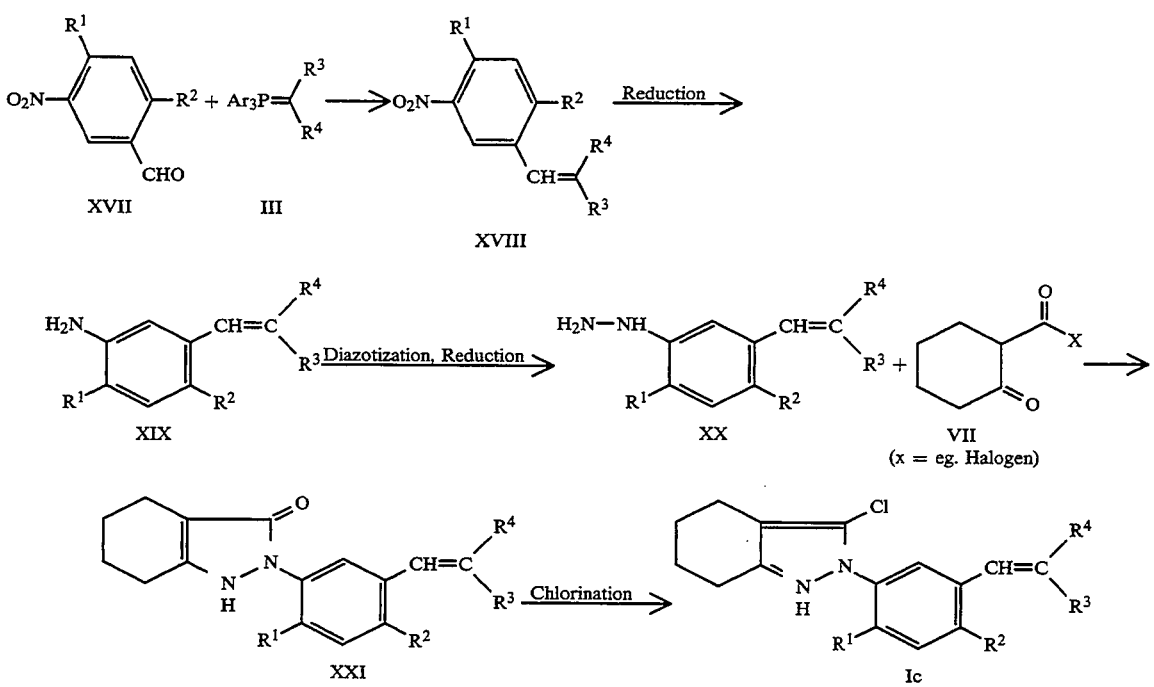

The reaction of the nitrobenzaldehydes XVII with the phosphoranes III is carried out by methods similar to those described above.

In the second stage of the reaction sequence, a nitrostyrene XVIII is reduced in a conventional manner with an inorganic compound such as a tin(II) salt, or iron or tin or by catalytic hydrogenation over a metal catalyst, such as Raney nickel, palladium or platinum, in an inert organic solvent to give the aniline derivative XIX.

Examples of suitable solvents for the reaction with inorganic compounds are alcohols, such as methanol, ethanol and isopropanol, and lower alkanoic acids, such as formic acid, acetic acid and propionic acid, and mixtures thereof. The reaction temperatures are from 25° to 150° C. preferably from 25° to 100° C.

If the reduction is carried out with hydrogen over a metal catalyst, solvents such as methanol or other alcohols, dimethylformamide, propionic acid, tetrahydrofuran and glacial acetic acid and mixtures thereof are suitable, the hydrogen pressure being from 1 to 150, preferably from 1 to 50, bar and the temperature from 25° to 100° C. preferably from 25° to 70° C.

The aniline derivative XIX thus obtained is then diazotized in a conventional manner in an inert solvent with an inorganic or organic nitrite to give the aryldiazonium salt, which is reduced in situ with an inorganic reducing agent to give the hydrazinc derivative XX.

The choice of the solvent depends on the type of nitrite.

Thus, inorganic nitrites, such as nitrous acid and alkali metal and alkaline earth metal salts thereof, are preferably used in aqueous solution in the presence of a mineral acid at −30° to 50° C., preferably from −10° to 5° C.

If organic nitrites, such as amyl nitrite, are used, aprotic solvents, such as toluene, are preferred. The reaction temperature in this case is from −10° to 25° C.

The subsequent reduction is carried out in situ using an inorganic reducing agent, such as a tin(II) salt, sodium dithionite, an alkali metal sulfite or bisulfite, such as sodium sulfite or sodium bisulfite, and/or sulfur dioxide. For solubilization, it may be advantageous to add a solvent such as glacial acetic acid, ethanol or toluene.

In the next reaction stage, the hydrazine derivative XX is cyclized in a conventional manner in an inert organic solvent at up to 200° C., preferably from 25° to 150° C., with a cyclohexanonecarboxylic acid derivative VII to give the indazole derivative XXI.

In formula VII, X is a nucleophilic leaving group, such as halogen, e.g. chlorine or bromine, or an alcoholate, such as methylate, ethylate, propylate, isopropylate or tosylate.

Preferably used solvents are, for example, lower alkanoic acids, such as acetic acid, or aprotic solvents, such as toluene and xylene. If X in formula VII is halogen, such as chlorine or bromine, it may be advantageous to carry out the reaction in the presence of a tertiary amine as a base. Examples of suitable bases for this purpose are triethylamine, diisopropylethylamine, N,N-dimethylaniline, N,N-dimethyl-p-aminopyridine, pyridine, isoquinoline, N-methylpyrrolidine, N,N,N′,N′-tetramethylethylenediamine, 1,5-diazabicyclo[4,3,0]non-5-ene and 1,8-diazabicyclo[5.4.0]undec-7-ene.

The indazole chloride Ic is obtained from this indazole derivative XXI in a conventional manner by reaction with a chlorinating agent conventionally used in organic chemistry, in the presence or absence of an inert organic solvent and in the presence or absence of a base.

Examples of suitable chlorinating agents are oxychlorides, such as phosphorus oxytrichloride, thionyl chloride and phosgene, trichloromethyl chloroformate or chlorides, such as phosphorus trichloride, phosphorus pentachloride and sulfur tetrachloride. Phosphorus oxytrichloride is preferably used.

The reaction can be carried out at from 25° to 200° C., preferably from 60° to 160° C., in the presence or absence of a base.

Bases which are suitable for this reaction are, for example, tertiary amines such as those stated above.

Suitable solvents here are, for example, aromatic hydrocarbons, such as toluene or xylene or chlorohydrocarbons, such as chloroform.

The compounds Id, e are also obtained, for example, by converting a derivative of the general formula XIX in a conventional manner (Houben-Weyl, Vol. IX, page 867 et seq. (1955)) in an inert organic solvent with thiophosgene into the corresponding isothiocyanate XXII, then subjecting the latter to an addition reaction with a tetrahydro- or perhydrodiazine derivative XII in an aprotic polar solvent and cyclizing the resulting thiourea XXIII with a phosgenating agent or thiophosgenating agent (Phos.) to give Id, e.

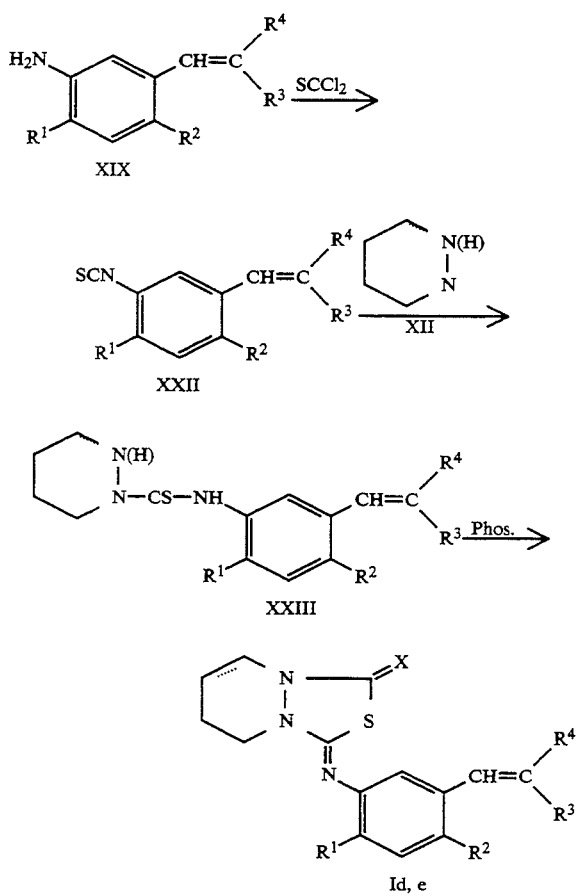

The reaction of the derivative XIX with thiophosgene is carried out as a rule at from −50° to 100° C., preferably from 0° to 50° C.

This reaction can be carried out both in a two-phase solvent system, such as methylene chloride/water, and in the presence of a base in an aprotic polar organic solvent.

In the last-mentioned case, the reaction is preferably carried out in toluene in the presence of an organic base, preferably a tertiary amine, such as triethylamine.

The anilines required for the reaction are obtained, for example, by reducing the corresponding nitro derivatives by methods similar to known ones (DE-A 37 24 399, DE-A 36 03 789).

The reaction of the isothiocyanates XXII with the piperazines XII is preferably carried out in an aprotic polar solvent, preferably an ether, in particular tetrahydrofuran, at from −50° to 100° C., preferably from 0° to 50° C.

The subsequent cyclization of thiourea XXIII with a phosgenating agent or thiophosgenating agent is effected, as a rule, at from 0° to 100° C., preferably from 20° to 70° C., in an aprotic polar solvent in the presence of a base.

Suitable phosgenating agents and thiophosgenating agents are in particular phosgene, thiophosgene and trichloromethyl chloroformate.

Preferably used solvents are ethers, halohydrocarbons and hydrocarbons, in particular halohydrocarbons, such as methylene chloride.

Suitable bases are tertiary amines, in particular pyridine.

The preparation of the styrene derivatives I may result in isomer mixtures which may be mixtures of enantiomers, of diastereomers or in particular of E/Z isomers. These mixtures can if desired be separated by the customary methods, for example by chromatography or by crystallization.

In view of the intended use of the compounds I as herbicides, preferred substituents are the following radicals: $R^1$ is hydrogen or halogen, such as fluorine, chlorine or bromine, in particular hydrogen or fluorine, $R^2$ is halogen, such as fluorine, chlorine or bromine, in particular chlorine, $R^3$ is hydrogen, halogen as stated under $R^2$, as well as iodine, in particular chlorine or bromine, or branched or straight-chain $C_1$–$C_4$-alkyl, such as methyl, ethyl, n-propyl, isopropyl, n-butyl, 1-methylpropyl, 2-methylpropyl or 1,1-dimethylethyl, in particular methyl or ethyl, $R^4$ is cyano, $C_1$–$C_6$-alkylcarbonyl, suitable alkyl radicals being methyl, ethyl, n-propyl, isopropyl, n-butyl, 1-methylpropyl, 2-methylpropyl, 1,1-dimethylethyl, n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl or 1-ethyl-2-methylpropyl, in particular methyl, ethyl, n-propyl or isopropyl, and $R^5$ and $R^6$ are each hydrogen, methyl or ethyl.

The styrene derivatives I may be present in the form of their agriculturally utilizable salts, those which are generally suitable being the salts of acids which do not impair the herbicidal action of I, for example alkali metal salts, in particular the sodium and potassium salts, alkaline earth metal salts, in particular the calcium, magnesium and barium salts, the manganese, copper, zinc and iron salts and also ammonium, phosphonium, sulfonium and sulfoxonium salts, for example the ammonium salts, tetraalkylammonium salts benzyltrialkylammonium salts, trialkylsulfonium salts and trialkylsulfoxonium salts.

The compounds I shown in Tables 1 to 5 below are mentioned by way of example.

TABLE 1

Styrene derivatives in which A = A₁

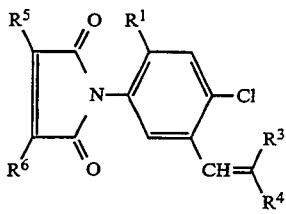

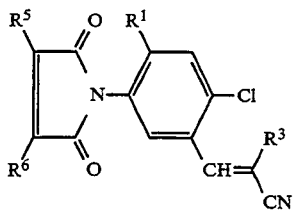

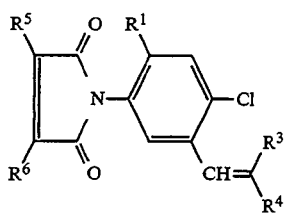

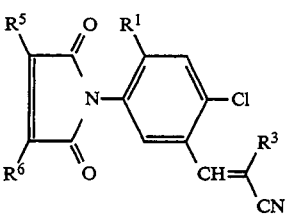

| R¹ | R³ | R⁴ | R⁵ | R⁶ |
|----|----|----|----|-----|
| H | H | CH₃ | H | H |
| H | H | CH₃ | H | CH₃ |
| H | H | CH₃ | H | C₂H₅ |
| H | H | CH₃ | CH₃ | H |
| H | H | CH₃ | CH₃ | CH₃ |
| H | H | CH₃ | CH₃ | C₂H₅ |
| H | H | CH₃ | C₂H₅ | H |
| H | H | CH₃ | C₂H₅ | CH₃ |
| H | H | CH₃ | C₂H₅ | C₂H₅ |
| H | H | C₂H₅ | H | H |
| H | H | C₂H₅ | H | CH₃ |
| H | H | C₂H₅ | H | C₂H₅ |
| H | H | C₂H₅ | CH₃ | H |
| H | H | C₂H₅ | CH₃ | CH₃ |
| H | H | C₂H₅ | CH₃ | C₂H₅ |
| H | H | C₂H₅ | C₂H₅ | H |
| H | H | C₂H₅ | C₂H₅ | CH₃ |
| H | H | C₂H₅ | C₂H₅ | C₂H₅ |
| H | H | i-C₃H₇ | H | H |
| H | H | i-C₃H₇ | H | CH₃ |
| H | H | i-C₃H₇ | H | C₂H₅ |
| H | H | i-C₃H₇ | CH₃ | H |
| H | H | i-C₃H₇ | CH₃ | CH₃ |
| H | H | i-C₃H₇ | CH₃ | C₂H₅ |
| H | H | i-C₃H₇ | C₂H₅ | H |
| H | H | i-C₃H₇ | C₂H₅ | CH₃ |
| H | H | i-C₃H₇ | C₂H₅ | C₂H₅ |
| H | H | n-C₆H₁₃ | H | H |
| H | H | n-C₆H₁₃ | H | CH₃ |
| H | H | n-C₆H₁₃ | H | C₂H₅ |
| H | H | n-C₆H₁₃ | CH₃ | H |
| H | H | n-C₆H₁₃ | CH₃ | CH₃ |
| H | H | n-C₆H₁₃ | CH₃ | C₂H₅ |
| H | H | n-C₆H₁₃ | C₂H₅ | H |
| H | H | n-C₆H₁₃ | C₂H₅ | CH₃ |
| H | H | n-C₆H₁₃ | C₂H₅ | C₂H₅ |
| H | Cl | CH₃ | H | H |
| H | Cl | CH₃ | H | CH₃ |
| H | Cl | CH₃ | H | C₂H₅ |
| H | Cl | CH₃ | CH₃ | H |
| H | Cl | CH₃ | CH₃ | CH₃ |
| H | Cl | CH₃ | CH₃ | C₂H₅ |
| H | Cl | CH₃ | C₂H₅ | H |
| H | Cl | CH₃ | C₂H₅ | CH₃ |
| H | Cl | CH₃ | C₂H₅ | C₂H₅ |
| H | Cl | C₂H₅ | H | H |
| H | Cl | C₂H₅ | H | CH₃ |
| H | Cl | C₂H₅ | H | C₂H₅ |
| H | Cl | C₂H₅ | CH₃ | H |
| H | Cl | C₂H₅ | CH₃ | CH₃ |
| H | Cl | C₂H₅ | CH₃ | C₂H₅ |
| H | Cl | C₂H₅ | C₂H₅ | H |
| H | Cl | C₂H₅ | C₂H₅ | CH₃ |
| H | Cl | C₂H₅ | C₂H₅ | C₂H₅ |
| H | Cl | i-C₃H₇ | H | H |
| H | Cl | i-C₃H₇ | H | CH₃ |
| H | Cl | i-C₃H₇ | H | C₂H₅ |
| H | Cl | i-C₃H₇ | CH₃ | H |
| H | Cl | i-C₃H₇ | CH₃ | CH₃ |
| H | Cl | i-C₃H₇ | CH₃ | C₂H₅ |
| H | Cl | i-C₃H₇ | C₂H₅ | H |
| H | Cl | i-C₃H₇ | C₂H₅ | CH₃ |
| H | Cl | i-C₃H₇ | C₂H₅ | C₂H₅ |
| H | Cl | n-C₆H₁₃ | H | H |
| H | Cl | n-C₆H₁₃ | H | CH₃ |
| H | Cl | n-C₆H₁₃ | H | C₂H₅ |
| H | Cl | n-C₆H₁₃ | CH₃ | H |
| H | Cl | n-C₆H₁₃ | CH₃ | CH₃ |
| H | Cl | n-C₆H₁₃ | CH₃ | C₂H₅ |
| H | Cl | n-C₆H₁₃ | C₂H₅ | H |
| H | Cl | n-C₆H₁₃ | C₂H₅ | CH₃ |
| H | Cl | n-C₆H₁₃ | C₂H₅ | C₂H₅ |
| H | Br | CH₃ | H | H |
| H | Br | CH₃ | H | CH₃ |
| H | Br | CH₃ | H | C₂H₅ |
| H | Br | CH₃ | CH₃ | H |
| H | Br | CH₃ | CH₃ | CH₃ |
| H | Br | CH₃ | CH₃ | C₂H₅ |
| H | Br | CH₃ | C₂H₅ | H |
| H | Br | CH₃ | C₂H₅ | CH₃ |
| H | Br | CH₃ | C₂H₅ | C₂H₅ |
| H | Br | C₂H₅ | H | H |
| H | Br | C₂H₅ | H | CH₃ |
| H | Br | C₂H₅ | H | C₂H₅ |
| H | Br | C₂H₅ | CH₃ | H |
| H | Br | C₂H₅ | CH₃ | CH₃ |
| H | Br | C₂H₅ | CH₃ | C₂H₅ |
| H | Br | C₂H₅ | C₂H₅ | H |
| H | Br | C₂H₅ | C₂H₅ | CH₃ |
| H | Br | C₂H₅ | C₂H₅ | C₂H₅ |
| H | Br | i-C₃H₇ | H | H |
| H | Br | i-C₃H₇ | H | CH₃ |
| H | Br | i-C₃H₇ | H | C₂H₅ |
| H | Br | i-C₃H₇ | CH₃ | H |
| H | Br | i-C₃H₇ | CH₃ | CH₃ |
| H | Br | i-C₃H₇ | CH₃ | C₂H₅ |
| H | Br | i-C₃H₇ | C₂H₅ | H |
| H | Br | i-C₃H₇ | C₂H₅ | CH₃ |
| H | Br | i-C₃H₇ | C₂H₅ | C₂H₅ |
| H | Br | n-C₆H₁₃ | H | H |
| H | Br | n-C₆H₁₃ | H | CH₃ |
| H | Br | n-C₆H₁₃ | H | C₂H₅ |
| H | Br | n-C₆H₁₃ | CH₃ | H |
| H | Br | n-C₆H₁₃ | CH₃ | CH₃ |
| H | Br | n-C₆H₁₃ | CH₃ | C₂H₅ |
| H | Br | n-C₆H₁₃ | C₂H₅ | H |
| H | Br | n-C₆H₁₃ | C₂H₅ | CH₃ |
| H | Br | n-C₆H₁₃ | C₂H₅ | C₂H₅ |
| H | I | CH₃ | H | H |
| H | I | CH₃ | H | CH₃ |
| H | I | CH₃ | H | C₂H₅ |
| H | I | CH₃ | CH₃ | H |
| H | I | CH₃ | CH₃ | CH₃ |
| H | I | CH₃ | CH₃ | C₂H₅ |

TABLE 1-continued

Styrene derivatives in which A = A₁

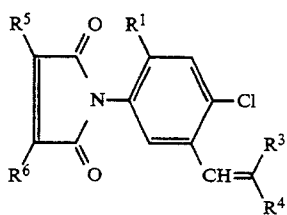

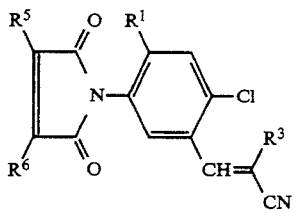

TABLE 1-continued

Styrene derivatives in which A = A₁

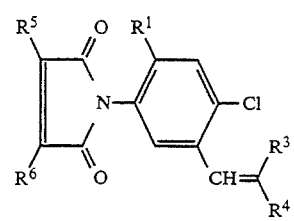

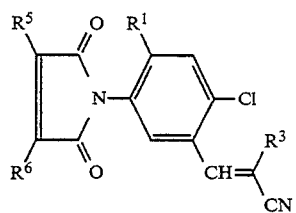

| R¹ | R³ | R⁴ | R⁵ | R⁶ | R¹ | R³ | R⁴ | R⁵ | R⁶ |
|---|---|---|---|---|---|---|---|---|---|
| H | I | CH₃ | C₂H₅ | H | H | CH₃ | n-C₆H₁₃ | H | H |
| H | I | CH₃ | C₂H₅ | CH₃ | H | CH₃ | n-C₆H₁₃ | H | CH₃ |
| H | I | CH₃ | C₂H₅ | C₂H₅ | H | CH₃ | n-C₆H₁₃ | H | C₂H₅ |
| H | I | C₂H₅ | H | H | H | CH₃ | n-C₆H₁₃ | CH₃ | H |
| H | I | C₂H₅ | H | CH₃ | H | CH₃ | n-C₆H₁₃ | CH₃ | CH₃ |
| H | I | C₂H₅ | H | C₂H₅ | H | CH₃ | n-C₆H₁₃ | CH₃ | C₂H₅ |
| H | I | C₂H₅ | CH₃ | H | H | CH₃ | n-C₆H₁₃ | C₂H₅ | H |
| H | I | C₂H₅ | CH₃ | CH₃ | H | CH₃ | n-C₆H₁₃ | C₂H₅ | CH₃ |
| H | I | C₂H₅ | CH₃ | C₂H₅ | H | CH₃ | n-C₆H₁₃ | C₂H₅ | C₂H₅ |
| H | I | C₂H₅ | C₂H₅ | H | F | H | CH₃ | H | H |
| H | I | C₂H₅ | C₂H₅ | CH₃ | F | H | CH₃ | H | CH₃ |
| H | I | C₂H₅ | C₂H₅ | C₂H₅ | F | H | CH₃ | H | C₂H₅ |
| H | I | i-C₃H₇ | H | H | F | H | CH₃ | CH₃ | H |
| H | I | i-C₃H₇ | H | CH₃ | F | H | CH₃ | CH₃ | CH₃ |
| H | I | i-C₃H₇ | H | C₂H₅ | F | H | CH₃ | CH₃ | C₂H₅ |
| H | I | i-C₃H₇ | CH₃ | H | F | H | CH₃ | C₂H₅ | H |
| H | I | i-C₃H₇ | CH₃ | CH₃ | F | H | CH₃ | C₂H₅ | CH₃ |
| H | I | i-C₃H₇ | CH₃ | C₂H₅ | F | H | CH₃ | C₂H₅ | C₂H₅ |
| H | I | i-C₃H₇ | C₂H₅ | H | F | H | C₂H₅ | H | H |
| H | I | i-C₃H₇ | C₂H₅ | CH₃ | F | H | C₂H₅ | H | CH₃ |
| H | I | i-C₃H₇ | C₂H₅ | C₂H₅ | F | H | C₂H₅ | H | C₂H₅ |
| H | I | n-C₆H₁₃ | H | H | F | H | C₂H₅ | CH₃ | H |
| H | I | n-C₆H₁₃ | H | CH₃ | F | H | C₂H₅ | CH₃ | CH₃ |
| H | I | n-C₆H₁₃ | H | C₂H₅ | F | H | C₂H₅ | CH₃ | C₂H₅ |
| H | I | n-C₆H₁₃ | CH₃ | H | F | H | C₂H₅ | C₂H₅ | H |
| H | I | n-C₆H₁₃ | CH₃ | CH₃ | F | H | C₂H₅ | C₂H₅ | CH₃ |
| H | I | n-C₆H₁₃ | CH₃ | C₂H₅ | F | H | C₂H₅ | C₂H₅ | C₂H₅ |
| H | I | n-C₆H₁₃ | C₂H₅ | H | F | H | i-C₃H₇ | H | H |
| H | I | n-C₆H₁₃ | C₂H₅ | CH₃ | F | H | i-C₃H₇ | H | CH₃ |
| H | I | n-C₆H₁₃ | C₂H₅ | C₂H₅ | F | H | i-C₃H₇ | H | C₂H₅ |
| H | CH₃ | CH₃ | H | H | F | H | i-C₃H₇ | CH₃ | H |
| H | CH₃ | CH₃ | H | CH₃ | F | H | i-C₃H₇ | CH₃ | CH₃ |
| H | CH₃ | CH₃ | H | C₂H₅ | F | H | i-C₃H₇ | CH₃ | C₂H₅ |
| H | CH₃ | CH₃ | CH₃ | H | F | H | i-C₃H₇ | C₂H₅ | H |
| H | CH₃ | CH₃ | CH₃ | CH₃ | F | H | i-C₃H₇ | C₂H₅ | CH₃ |
| H | CH₃ | CH₃ | CH₃ | C₂H₅ | F | H | i-C₃H₇ | C₂H₅ | C₂H₅ |
| H | CH₃ | CH₃ | C₂H₅ | H | F | H | n-C₆H₁₃ | H | H |
| H | CH₃ | CH₃ | C₂H₅ | CH₃ | F | H | n-C₆H₁₃ | H | CH₃ |
| H | CH₃ | CH₃ | C₂H₅ | C₂H₅ | F | H | n-C₆H₁₃ | H | C₂H₅ |
| H | CH₃ | C₂H₅ | H | H | F | H | n-C₆H₁₃ | CH₃ | H |
| H | CH₃ | C₂H₅ | H | CH₃ | F | H | n-C₆H₁₃ | CH₃ | CH₃ |
| H | CH₃ | C₂H₅ | H | C₂H₅ | F | H | n-C₆H₁₃ | CH₃ | C₂H₅ |
| H | CH₃ | C₂H₅ | CH₃ | H | F | H | n-C₆H₁₃ | C₂H₅ | H |
| H | CH₃ | C₂H₅ | CH₃ | CH₃ | F | H | n-C₆H₁₃ | C₂H₅ | CH₃ |
| H | CH₃ | C₂H₅ | CH₃ | C₂H₅ | F | H | n-C₆H₁₃ | C₂H₅ | C₂H₅ |
| H | CH₃ | C₂H₅ | C₂H₅ | H | F | Cl | CH₃ | H | H |
| H | CH₃ | C₂H₅ | C₂H₅ | CH₃ | F | Cl | CH₃ | H | CH₃ |
| H | CH₃ | C₂H₅ | C₂H₅ | C₂H₅ | F | Cl | CH₃ | H | C₂H₅ |
| H | CH₃ | i-C₃H₇ | H | H | F | Cl | CH₃ | CH₃ | H |
| H | CH₃ | i-C₃H₇ | H | CH₃ | F | Cl | CH₃ | CH₃ | CH₃ |
| H | CH₃ | i-C₃H₇ | H | C₂H₅ | F | Cl | CH₃ | CH₃ | C₂H₅ |
| H | CH₃ | i-C₃H₇ | CH₃ | H | F | Cl | CH₃ | C₂H₅ | H |
| H | CH₃ | i-C₃H₇ | CH₃ | CH₃ | F | Cl | CH₃ | C₂H₅ | CH₃ |
| H | CH₃ | i-C₃H₇ | CH₃ | C₂H₅ | F | Cl | CH₃ | C₂H₅ | C₂H₅ |
| H | CH₃ | i-C₃H₇ | C₂H₅ | H | F | Cl | C₂H₅ | H | H |
| H | CH₃ | i-C₃H₇ | C₂H₅ | CH₃ | F | Cl | C₂H₅ | H | CH₃ |
| H | CH₃ | i-C₃H₇ | C₂H₅ | C₂H₅ | F | Cl | C₂H₅ | H | C₂H₅ |

TABLE 1-continued

Styrene derivatives in which A = A₁

(Structures shown: maleimide-substituted chloroaniline with styryl group, R³/R⁴ on vinyl; and cyano-substituted variant)

| R¹ | R³ | R⁴ | R⁵ | R⁶ |
|---|---|---|---|---|
| F | Cl | C₂H₅ | CH₃ | H |
| F | Cl | C₂H₅ | CH₃ | CH₃ |
| F | Cl | C₂H₅ | CH₃ | C₂H₅ |
| F | Cl | C₂H₅ | C₂H₅ | H |
| F | Cl | C₂H₅ | C₂H₅ | CH₃ |
| F | Cl | C₂H₅ | C₂H₅ | C₂H₅ |
| F | Cl | i-C₃H₇ | H | H |
| F | Cl | i-C₃H₇ | H | CH₃ |
| F | Cl | i-C₃H₇ | H | C₂H₅ |
| F | Cl | i-C₃H₇ | CH₃ | H |
| F | Cl | i-C₃H₇ | CH₃ | CH₃ |
| F | Cl | i-C₃H₇ | CH₃ | C₂H₅ |
| F | Cl | i-C₃H₇ | C₂H₅ | H |
| F | Cl | i-C₃H₇ | C₂H₅ | CH₃ |
| F | Cl | i-C₃H₇ | C₂H₅ | C₂H₅ |
| F | Cl | n-C₆H₁₃ | H | H |
| F | Cl | n-C₆H₁₃ | H | CH₃ |
| F | Cl | n-C₆H₁₃ | H | C₂H₅ |
| F | Cl | n-C₆H₁₃ | CH₃ | H |
| F | Cl | n-C₆H₁₃ | CH₃ | CH₃ |
| F | Cl | n-C₆H₁₃ | CH₃ | C₂H₅ |
| F | Cl | n-C₆H₁₃ | C₂H₅ | H |
| F | Cl | n-C₆H₁₃ | C₂H₅ | CH₃ |
| F | Cl | n-C₆H₁₃ | C₂H₅ | C₂H₅ |
| F | Br | CH₃ | H | H |
| F | Br | CH₃ | H | CH₃ |
| F | Br | CH₃ | H | C₂H₅ |
| F | Br | CH₃ | CH₃ | H |
| F | Br | CH₃ | CH₃ | CH₃ |
| F | Br | CH₃ | CH₃ | C₂H₅ |
| F | Br | CH₃ | C₂H₅ | H |
| F | Br | CH₃ | C₂H₅ | CH₃ |
| F | Br | CH₃ | C₂H₅ | C₂H₅ |
| F | Br | C₂H₅ | H | H |
| F | Br | C₂H₅ | H | CH₃ |
| F | Br | C₂H₅ | H | C₂H₅ |
| F | Br | C₂H₅ | CH₃ | H |
| F | Br | C₂H₅ | CH₃ | CH₃ |
| F | Br | C₂H₅ | CH₃ | C₂H₅ |
| F | Br | C₂H₅ | C₂H₅ | H |
| F | Br | C₂H₅ | C₂H₅ | CH₃ |
| F | Br | C₂H₅ | C₂H₅ | C₂H₅ |
| F | Br | i-C₃H₇ | H | H |
| F | Br | i-C₃H₇ | H | CH₃ |
| F | Br | i-C₃H₇ | H | C₂H₅ |
| F | Br | i-C₃H₇ | CH₃ | H |
| F | Br | i-C₃H₇ | CH₃ | CH₃ |
| F | Br | i-C₃H₇ | CH₃ | C₂H₅ |
| F | Br | i-C₃H₇ | C₂H₅ | H |
| F | Br | i-C₃H₇ | C₂H₅ | CH₃ |
| F | Br | i-C₃H₇ | C₂H₅ | C₂H₅ |
| F | Br | n-C₆H₁₃ | H | H |
| F | Br | n-C₆H₁₃ | H | CH₃ |
| F | Br | n-C₆H₁₃ | H | C₂H₅ |
| F | Br | n-C₆H₁₃ | CH₃ | H |
| F | Br | n-C₆H₁₃ | CH₃ | CH₃ |
| F | Br | n-C₆H₁₃ | CH₃ | C₂H₅ |
| F | Br | n-C₆H₁₃ | C₂H₅ | H |
| F | Br | n-C₆H₁₃ | C₂H₅ | CH₃ |
| F | Br | n-C₆H₁₃ | C₂H₅ | C₂H₅ |
| F | I | CH₃ | H | H |
| F | I | CH₃ | H | CH₃ |
| F | I | CH₃ | H | C₂H₅ |
| F | I | CH₃ | CH₃ | H |
| F | I | CH₃ | CH₃ | CH₃ |
| F | I | CH₃ | CH₃ | C₂H₅ |
| F | I | CH₃ | C₂H₅ | H |
| F | I | CH₃ | C₂H₅ | CH₃ |
| F | I | CH₃ | C₂H₅ | C₂H₅ |
| F | I | C₂H₅ | H | H |
| F | I | C₂H₅ | H | CH₃ |
| F | I | C₂H₅ | H | C₂H₅ |
| F | I | C₂H₅ | CH₃ | H |
| F | I | C₂H₅ | CH₃ | CH₃ |
| F | I | C₂H₅ | CH₃ | C₂H₅ |
| F | I | C₂H₅ | C₂H₅ | H |
| F | I | C₂H₅ | C₂H₅ | CH₃ |
| F | I | C₂H₅ | C₂H₅ | C₂H₅ |
| F | I | i-C₃H₇ | H | H |
| F | I | i-C₃H₇ | H | CH₃ |
| F | I | i-C₃H₇ | H | C₂H₅ |
| F | I | i-C₃H₇ | CH₃ | H |
| F | I | i-C₃H₇ | CH₃ | CH₃ |
| F | I | i-C₃H₇ | CH₃ | C₂H₅ |
| F | I | i-C₃H₇ | C₂H₅ | H |
| F | I | i-C₃H₇ | C₂H₅ | CH₃ |
| F | I | i-C₃H₇ | C₂H₅ | C₂H₅ |
| F | I | n-C₆H₁₃ | H | H |
| F | I | n-C₆H₁₃ | H | CH₃ |
| F | I | n-C₆H₁₃ | H | C₂H₅ |
| F | I | n-C₆H₁₃ | CH₃ | H |
| F | I | n-C₆H₁₃ | CH₃ | CH₃ |
| F | I | n-C₆H₁₃ | CH₃ | C₂H₅ |
| F | I | n-C₆H₁₃ | C₂H₅ | H |
| F | I | n-C₆H₁₃ | C₂H₅ | CH₃ |
| F | I | n-C₆H₁₃ | C₂H₅ | C₂H₅ |
| F | CH₃ | CH₃ | H | H |
| F | CH₃ | CH₃ | H | CH₃ |
| F | CH₃ | CH₃ | H | C₂H₅ |
| F | CH₃ | CH₃ | CH₃ | H |
| F | CH₃ | CH₃ | CH₃ | CH₃ |
| F | CH₃ | CH₃ | CH₃ | C₂H₅ |
| F | CH₃ | CH₃ | C₂H₅ | H |
| F | CH₃ | CH₃ | C₂H₅ | CH₃ |
| F | CH₃ | CH₃ | C₂H₅ | C₂H₅ |
| F | CH₃ | C₂H₅ | H | H |
| F | CH₃ | C₂H₅ | H | CH₃ |
| F | CH₃ | C₂H₅ | H | C₂H₅ |
| F | CH₃ | C₂H₅ | CH₃ | H |
| F | CH₃ | C₂H₅ | CH₃ | CH₃ |
| F | CH₃ | C₂H₅ | CH₃ | C₂H₅ |
| F | CH₃ | C₂H₅ | C₂H₅ | H |
| F | CH₃ | C₂H₅ | C₂H₅ | CH₃ |
| F | CH₃ | C₂H₅ | C₂H₅ | C₂H₅ |

TABLE 1-continued
Styrene derivatives in which A = A₁

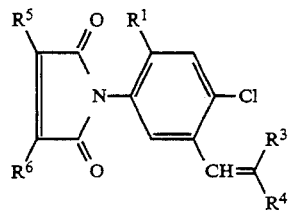

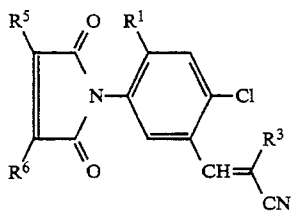

| R¹ | R³ | R⁴ | R⁵ | R⁶ |
|---|---|---|---|---|
| F | CH₃ | i-C₃H₇ | H | H |
| F | CH₃ | i-C₃H₇ | H | CH₃ |
| F | CH₃ | i-C₃H₇ | H | C₂H₅ |
| F | CH₃ | i-C₃H₇ | CH₃ | H |
| F | CH₃ | i-C₃H₇ | CH₃ | CH₃ |
| F | CH₃ | i-C₃H₇ | CH₃ | C₂H₅ |
| F | CH₃ | i-C₃H₇ | C₂H₅ | H |
| F | CH₃ | i-C₃H₇ | C₂H₅ | CH₃ |
| F | CH₃ | i-C₃H₇ | C₂H₅ | C₂H₅ |
| F | CH₃ | n-C₆H₁₃ | H | H |
| F | CH₃ | n-C₆H₁₃ | H | CH₃ |
| F | CH₃ | n-C₆H₁₃ | H | C₂H₅ |
| F | CH₃ | n-C₆H₁₃ | CH₃ | H |
| F | CH₃ | n-C₆H₁₃ | CH₃ | CH₃ |
| F | CH₃ | n-C₆H₁₃ | CH₃ | C₂H₅ |
| F | CH₃ | n-C₆H₁₃ | C₂H₅ | H |
| F | CH₃ | n-C₆H₁₃ | C₂H₅ | CH₃ |
| F | CH₃ | n-C₆H₁₃ | C₂H₅ | C₂H₅ |

TABLE 2
Styrene derivatives in which A = A₂

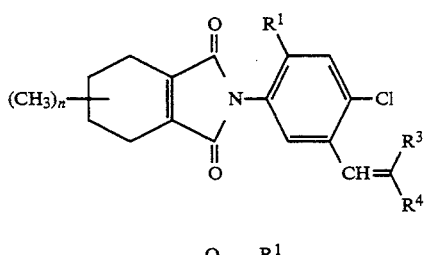

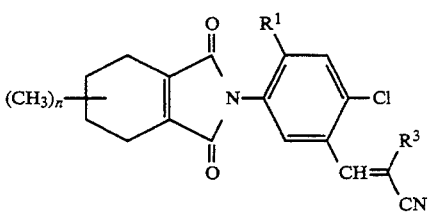

| R¹ | R³ | R⁴ | n |
|---|---|---|---|
| H | H | CO—CH₃ | 0 |
| H | H | CO—CH₃ | 1 |
| H | H | CO—C₂H₅ | 0 |
| H | H | CO—C₂H₅ | 1 |
| H | H | CO-n-C₃H₇ | 0 |
| H | H | CO-n-C₃H₇ | 1 |
| H | H | CO—CH(CH₃)—C₃H₇ | 0 |

TABLE 2-continued
Styrene derivatives in which A = A₂

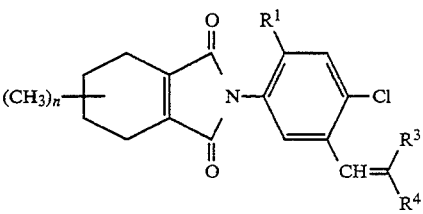

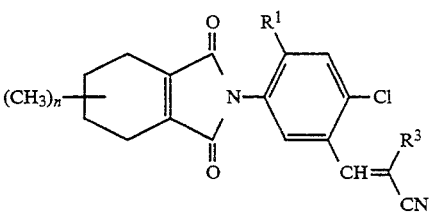

| R¹ | R³ | R⁴ | n |
|---|---|---|---|
| H | H | CO—CH(CH₃)—C₃H₇ | 1 |
| H | Cl | CO—CH₃ | 0 |
| H | Cl | CO—CH₃ | 1 |
| H | Cl | CO—C₂H₅ | 0 |
| H | Cl | CO—C₂H₅ | 1 |
| H | Cl | CO-n-C₃H₇ | 0 |
| H | Cl | CO-n-C₃H₇ | 1 |
| H | Cl | CO—CH(CH₃)—C₃H₇ | 0 |
| H | Cl | CO—CH(CH₃)—C₃H₇ | 1 |
| H | Br | CO—CH₃ | 0 |
| H | Br | CO—CH₃ | 1 |
| H | Br | CO—C₂H₅ | 0 |
| H | Br | CO—C₂H₅ | 1 |
| H | Br | CO-n-C₃H₇ | 0 |
| H | Br | CO-n-C₃H₇ | 1 |
| H | Br | CO—CH(CH₃)—C₃H₇ | 0 |
| H | Br | CO—CH(CH₃)—C₃H₇ | 1 |
| H | I | CO—CH₃ | 0 |
| H | I | CO—CH₃ | 1 |
| H | I | CO—C₂H₅ | 0 |
| H | I | CO—C₂H₅ | 1 |
| H | I | CO-n-C₃H₇ | 0 |
| H | I | CO-n-C₃H₇ | 1 |
| H | I | CO—CH(CH₃)—C₃H₇ | 0 |
| H | I | CO—CH(CH₃)—C₃H₇ | 1 |
| H | CH₃ | CO—CH₃ | 0 |
| H | CH₃ | CO—CH₃ | 1 |
| H | CH₃ | CO—C₂H₅ | 0 |
| H | CH₃ | CO—C₂H₅ | 1 |
| H | CH₃ | CO-n-C₃H₇ | 0 |
| H | CH₃ | CO-n-C₃H₇ | 1 |

TABLE 2-continued

Styrene derivatives in which A = A₂

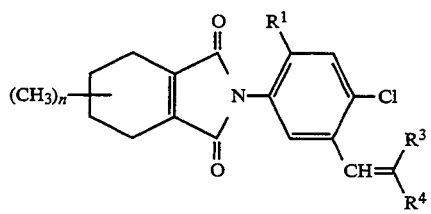

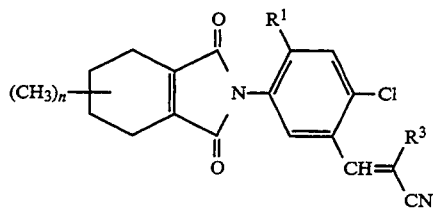

| R¹ | R³ | R⁴ | n |
|---|---|---|---|
| H | CH₃ | CO—CH(CH₃)—C₃H₇ | 0 |
| H | CH₃ | CO—CH(CH₃)—C₃H₇ | 1 |
| F | H | CO—CH₃ | 0 |
| F | H | CO—CH₃ | 1 |
| F | H | CO—C₂H₅ | 0 |
| F | H | CO—C₂H₅ | 1 |
| F | H | CO-n-C₃H₇ | 0 |
| F | H | CO-n-C₃H₇ | 1 |
| F | H | CO—CH(CH₃)—C₃H₇ | 0 |
| F | H | CO—CH(CH₃)—C₃H₇ | 1 |
| F | Cl | CO—CH₃ | 0 |
| F | Cl | CO—CH₃ | 1 |
| F | Cl | CO—C₂H₅ | 0 |
| F | Cl | CO—C₂H₅ | 1 |
| F | Cl | CO-n-C₃H₇ | 0 |
| F | Cl | CO-n-C₃H₇ | 1 |
| F | Cl | CO—CH(CH₃)—C₃H₇ | 0 |
| F | Cl | CO—CH(CH₃)—C₃H₇ | 1 |
| F | Br | CO—CH₃ | 0 |
| F | Br | CO—CH₃ | 1 |
| F | Br | CO—C₂H₅ | 0 |
| F | Br | CO—C₂H₅ | 1 |
| F | Br | CO-n-C₃H₇ | 0 |
| F | Br | CO-n-C₃H₇ | 1 |
| F | Br | CO—CH(CH₃)—C₃H₇ | 0 |
| F | Br | CO—CH(CH₃)—C₃H₇ | 1 |
| F | I | CO—CH₃ | 0 |
| F | I | CO—CH₃ | 1 |
| F | I | CO—C₂H₅ | 0 |
| F | I | CO—C₂H₅ | 1 |
| F | I | CO-n-C₃H₇ | 0 |

TABLE 2-continued

Styrene derivatives in which A = A₂

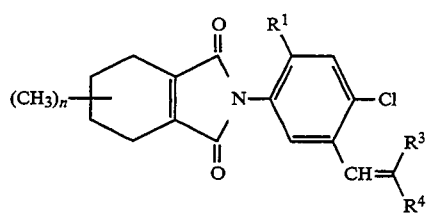

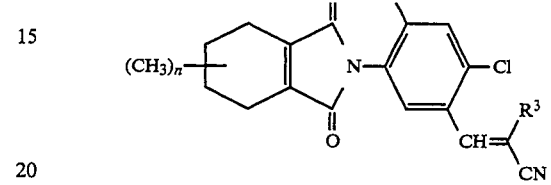

| R¹ | R³ | R⁴ | n |
|---|---|---|---|
| F | I | CO-n-C₃H₇ | 1 |
| F | I | CO—CH(CH₃)—C₃H₇ | 0 |
| F | I | CO—CH(CH₃)—C₃H₇ | 1 |
| F | CH₃ | CO—CH₃ | 0 |
| F | CH₃ | CO—CH₃ | 1 |
| F | CH₃ | CO—C₂H₅ | 0 |
| F | CH₃ | CO—C₂H₅ | 1 |
| F | CH₃ | CO-n-C₃H₇ | 0 |
| F | CH₃ | CO-n-C₃H₇ | 1 |
| F | CH₃ | CO—CH(CH₃)—C₃H₇ | 0 |
| F | CH₃ | CO—CH(CH₃)—C₃H₇ | 1 |

TABLE 3

Styrene derivatives in which A = A₃

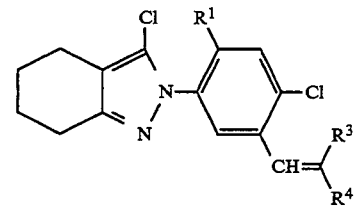

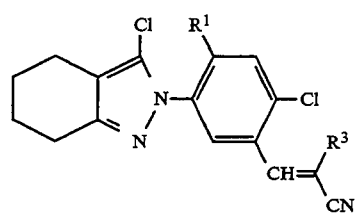

| R¹ | R³ | R⁴ |
|---|---|---|
| H | H | CH₃ |
| H | H | C₂H₅ |
| H | H | sec-C₄H₉ |
| H | H | n-C₆H₁₃ |

TABLE 3-continued

Styrene derivatives in which A = A₃

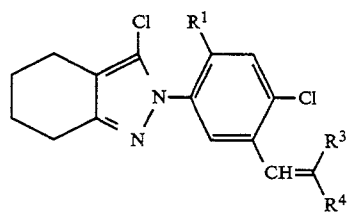

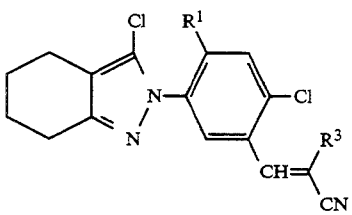

| R¹ | R³ | R⁴ |
|---|---|---|
| H | Cl | CH₃ |
| H | Cl | C₂H₅ |
| H | Cl | sec-C₄H₉ |
| H | Cl | n-C₆H₁₃ |
| H | Br | CH₃ |
| H | Br | C₂H₅ |
| H | Br | sec-C₄H₉ |
| H | Br | n-C₆H₁₃ |
| H | I | CH₃ |
| H | I | C₂H₅ |
| H | I | sec-C₄H₉ |
| H | I | n-C₆H₁₃ |
| H | CH₃ | CH₃ |
| H | CH₃ | C₂H₅ |
| H | CH₃ | sec-C₄H₉ |
| H | CH₃ | n-C₆H₁₃ |
| F | H | CH₃ |
| F | H | C₂H₅ |
| F | H | sec-C₄H₉ |
| F | H | n-C₆H₁₃ |
| F | Cl | CH₃ |
| F | Cl | C₂H₅ |
| F | Cl | sec-C₄H₉ |
| F | Cl | n-C₆H₁₃ |
| F | Br | CH₃ |
| F | Br | C₂H₅ |
| F | Br | sec-C₄H₉ |
| F | Br | n-C₆H₁₃ |
| F | I | CH₃ |
| F | I | C₂H₅ |
| F | I | sec-C₄H₉ |
| F | I | n-C₆H₁₃ |
| F | CH₃ | CH₃ |
| F | CH₃ | C₂H₅ |
| F | CH₃ | sec-C₄H₉ |
| F | CH₃ | n-C₆H₁₃ |

TABLE 4

Styrene derivatives in which A = A₄ and R⁴ = alkylcarbonyl

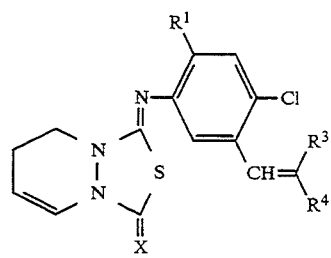

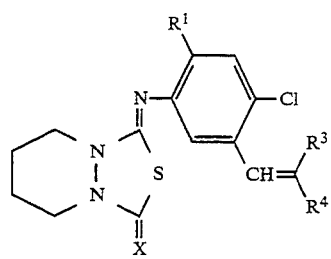

| R¹ | R³ | R⁴ | X |
|---|---|---|---|
| H | H | CO—CH₃ | O |
| H | H | CO—CH₃ | S |
| H | H | CO—C₂H₅ | O |
| H | H | CO—C₂H₅ | S |
| H | H | CO-i-C₃H₇ | O |
| H | H | CO-i-C₃H₇ | S |
| H | H | CO-n-C₅H₁₁ | O |
| H | H | CO-n-C₅H₁₁ | S |
| H | Cl | CO—CH₃ | O |
| H | Cl | CO—CH₃ | S |
| H | Cl | CO—C₂H₅ | O |
| H | Cl | CO—C₂H₅ | S |
| H | Cl | CO-i-C₃H₇ | O |
| H | Cl | CO-i-C₃H₇ | S |
| H | Cl | CO-n-C₅H₁₁ | O |
| H | Cl | CO-n-C₅H₁₁ | S |
| H | Br | CO—CH₃ | O |
| H | Br | CO—CH₃ | S |
| H | Br | CO—C₂H₅ | O |
| H | Br | CO—C₂H₅ | S |
| H | Br | CO-i-C₃H₇ | O |
| H | Br | CO-i-C₃H₇ | S |
| H | Br | CO-n-C₅H₁₁ | O |
| H | Br | CO-n-C₅H₁₁ | S |
| H | I | CO—CH₃ | O |
| H | I | CO—CH₃ | S |
| H | I | CO—C₂H₅ | O |
| H | I | CO—C₂H₅ | S |
| H | I | CO-i-C₃H₇ | O |
| H | I | CO-i-C₃H₇ | S |
| H | I | CO-n-C₅H₁₁ | O |
| H | I | CO-n-C₅H₁₁ | S |
| H | CH₃ | CO—CH₃ | O |
| H | CH₃ | CO—CH₃ | S |
| H | CH₃ | CO—C₂H₅ | O |
| H | CH₃ | CO—C₂H₅ | S |
| H | CH₃ | CO-i-C₃H₇ | O |
| H | CH₃ | CO-i-C₃H₇ | S |
| H | CH₃ | CO-n-C₅H₁₁ | O |
| H | CH₃ | CO-n-C₅H₁₁ | S |
| F | H | CO—CH₃ | O |
| F | H | CO—CH₃ | S |
| F | H | CO—C₂H₅ | O |
| F | H | CO—C₂H₅ | S |
| F | H | CO-i-C₃H₇ | O |
| F | H | CO-i-C₃H₇ | S |
| F | H | CO-n-C₅H₁₁ | O |
| F | H | CO-n-C₅H₁₁ | S |
| F | Cl | CO—CH₃ | O |
| F | Cl | CO—CH₃ | S |
| F | Cl | CO—C₂H₅ | O |
| F | Cl | CO—C₂H₅ | S |

TABLE 4-continued

Styrene derivatives in which A = A4 and R⁴ = alkylcarbonyl

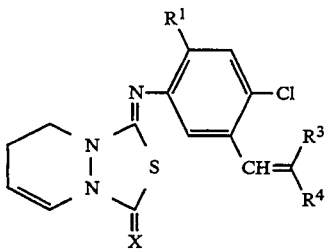

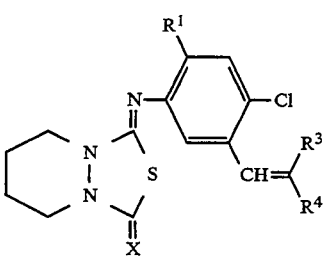

| R¹ | R³ | R⁴ | X |
|---|---|---|---|
| F | Cl | CO-i-C₃H₇ | O |
| F | Cl | CO-i-C₃H₇ | S |
| F | Cl | CO-n-C₅H₁₁ | O |
| F | Cl | CO-n-C₅H₁₁ | S |
| F | Br | CO—CH₃ | O |
| F | Br | CO—CH₃ | S |
| F | Br | CO—C₂H₅ | O |
| F | Br | CO—C₂H₅ | S |
| F | Br | CO-i-C₃H₇ | O |
| F | Br | CO-i-C₃H₇ | S |
| F | Br | CO-n-C₅H₁₁ | O |
| F | Br | CO-n-C₅H₁₁ | S |
| F | I | CO—CH₃ | O |
| F | I | CO—CH₃ | S |
| F | I | CO—C₂H₅ | O |
| F | I | CO—C₂H₅ | S |
| F | I | CO-i-C₃H₇ | O |
| F | I | CO-i-C₃H₇ | S |
| F | I | CO-n-C₅H₁₁ | O |
| F | I | CO-n-C₅H₁₁ | S |
| F | CH₃ | CO—CH₃ | O |
| F | CH₃ | CO—CH₃ | S |
| F | CH₃ | CO—C₂H₅ | O |
| F | CH₃ | CO—C₂H₅ | S |
| F | CH₃ | CO-i-C₃H₇ | O |
| F | CH₃ | CO-i-C₃H₇ | S |
| F | CH₃ | CO-n-C₅H₁₁ | O |
| F | CH₃ | CO-n-C₅H₁₁ | S |

TABLE 5

Styrene derivatives in which A = A4 and R⁴ = cyano

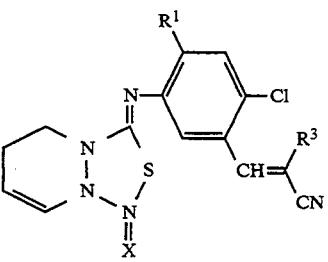

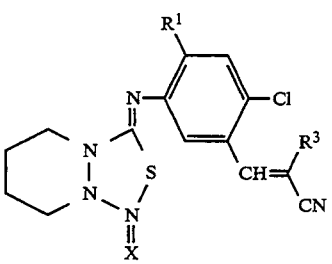

| R¹ | R³ | X |
|---|---|---|
| H | H | O |
| H | H | S |
| H | H | O |
| H | H | S |
| H | H | O |
| H | H | S |
| H | Cl | O |
| H | Cl | S |
| H | Cl | O |
| H | Cl | S |
| H | Cl | O |
| H | Cl | S |
| H | Br | O |
| H | Br | S |
| H | Br | O |
| H | Br | S |
| H | Br | O |
| H | Br | S |
| H | I | O |
| H | I | S |
| H | I | O |
| H | I | S |
| H | I | O |
| H | I | S |
| H | CH₃ | O |
| H | CH₃ | S |
| H | CH₃ | O |
| H | CH₃ | S |
| H | CH₃ | O |
| H | CH₃ | S |
| F | H | O |
| F | H | S |
| F | H | O |
| F | H | S |
| F | H | O |
| F | H | S |
| F | Cl | O |
| F | Cl | S |
| F | Cl | O |

TABLE 5-continued

Styrene derivatives in which A = A4 and $R^4$ = cyano

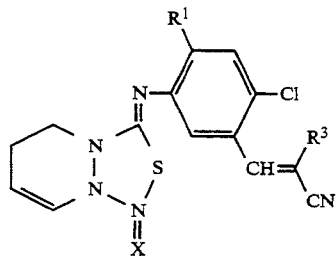

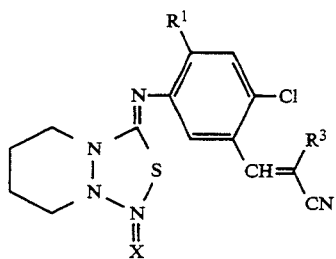

| $R^1$ | $R^3$ | X |
|---|---|---|
| F | Cl | S |
| F | Cl | O |
| F | Cl | S |
| F | Cl | O |
| F | Cl | S |
| F | Br | O |
| F | Br | S |
| F | Br | O |
| F | Br | S |
| F | Br | O |
| F | Br | S |
| F | Br | O |
| F | Br | S |
| F | I | O |
| F | I | S |
| F | I | O |
| F | I | S |
| F | I | O |
| F | I | S |
| F | I | O |
| F | I | S |
| F | $CH_3$ | O |
| F | $CH_3$ | S |
| F | $CH_3$ | O |
| F | $CH_3$ | S |
| F | $CH_3$ | O |
| F | $CH_3$ | S |
| F | $CH_3$ | O |
| F | $CH_3$ | S |

The styrene derivatives I, both in the form of isomer mixtures and as the pure isomers, can be used as herbicides. The compounds I and the herbicides and defoliants containing them can be applied, for example, in the form of directly sprayable solutions, powders, suspensions, including concentrated aqueous, oily or other suspensions or dispersions, emulsions, oil dispersions, pastes, dusting agents, broadcasting agents or granules, by spraying, atomizing, dusting, broadcasting or pouring. The application forms depend on the intended uses; they should in any case ensure very fine distribution of the novel active ingredients.

The styrene derivatives I are suitable in general for the preparation of directly sprayable solutions, emulsions, pastes or oil dispersions. Suitable inert additives are mineral oil fractions having a medium to high boiling point, such as kerosene or diesel oil, as well as coal tar oils and oils of vegetable or animal origin, aliphatic, cyclic and aromatic hydrocarbons, e.g. toluene, xylene, paraffin, tetrahydronaphthalene, alkylated naphthalenes or derivatives thereof, methanol, ethanol, propanol, butanol, cyclohexanol, cyclohexanone, chlorobenzene, isophorone or strongly polar solvents, such as N,N-dimethylformamide, dimethyl sulfoxide, N-methylpyrrolidone or water.

Aqueous application forms can be prepared from emulsion concentrates, dispersions, pastes, wettable powders or water-dispersible granules by adding water. For the preparation of emulsions, pastes or oil dispersions, the substrates as such or in solution in an oil or solvent can be homogenized in water by means of wetting agents, adherents, dispersants or emulsifiers. However, it is also possible to prepare concentrates which consist of active substance, wetting agents, adherents, dispersants or emulsifiers and possibly solvents or oil and which are suitable for dilution with water.

Suitable surfactants are alkali metal, alkaline earth metal and ammonium salts of aromatic sulfonic acids, for example lignin-, phenol-, naphthalene- and dibutyl-naphthalenesulfonic acid, and of fatty acids, alkyl- and alkylarylsulfonates, alkyl, lauryl ether and fatty alcohol sulfates, and salts of sulfated hexa-, hepta- and octadecanols, and of fatty alcohol glycol ethers, condensates of sulfonated naphthalene and its derivatives with formaldehyde, condensates of naphthalene or of naphthalenesulfonic acids with phenol and formaldehyde, polyoxyethylene octylphenol ethers, ethoxylated isooctyl-, octyl- or nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene, lauryl alcohol polyglycol ether acetate, sorbitol esters, ligninsulfite waste liquors or methylcellulose.

Powders, broadcasting agents and dusting agents can be prepared by mixing or milling the active substances together with a solid carrier.

Granules, for example coated, impregnated and homogeneous granules, can be prepared by binding the active ingredients to solid carriers. Solid carriers are mineral earths, such as silica gel, silicas, silicates, talc, kaolin, limestone, lime, chalk, bole, loess, clay, dolomite, kieselguhr, calcium sulfate, magnesium sulfate, magnesium oxide, milled plastics, fertilizers, such as ammonium sulfate, ammonium phosphate, ammonium nitrate and ureas, and vegetable products, such as grain flours, bark meal, wood meal, nutshell meal, cellulosic powders and other solid carriers.

The formulations contain from 0.01 to 95, preferably from 0.5 to 90, % by weight of active ingredients. The active ingredients are used in a purity of from 90 to 100% preferably from 95 to 100% (according to the NMR spectrum).

The novel compounds I can be formulated, for example, as follows:

I. 90 parts by weight of compound No. 02 are mixed with 10 parts by weight of N-methyl-α-pyrrolidone, and a solution which is suitable for use in the form of very small drops is obtained.

II. 20 parts by weight of compound No. 03 are dissolved in a mixture which consists of 80 parts by weight of xylene, 10 parts by weight of the adduct of from 8 to 10 mol of ethylene oxide with 1 mol of N-(hydroxyethyl)-oleamide, 5 parts by weight of the calcium salt of dodecylbenzenesulfonic acid and 5 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

III. 20 parts by weight of compound No. 06 are dissolved in a mixture which consists of 40 parts by weight of cyclohexanone, 30 parts by weight of isobutanol, 20 parts by weight of the adduct of 7 mol of ethylene oxide with 1 mol of isooctylphenol and 10 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

IV. 20 parts by weight of active ingredient No. 10 are dissolved in a mixture which consists of 25 parts by weight of cyclohexanone, 65 parts by weight of a mineral oil fraction boiling within a range from 210° to 280° C. and 10 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

V. 20 parts by weight of active ingredient No. 12 are thoroughly mixed with 3 parts by weight of the sodium salt of diisobutylnaphthalene-α-sulfonic acid, 17 parts by weight of the sodium salt of a ligninsulfonic acid obtained from a sulfite waste liquor and 60 parts by weight of silica gel powder, and the mixture is milled in a hammer mill. By finely distributing the mixture in 20,000 parts by weight of water, a spray liquor which contains 0.1% by weight of the active ingredient is obtained.

VI. 3 parts by weight of active ingredient No. 14 are mixed with 97 parts by weight of finely divided kaolin. A dusting agent which contains 3% by weight of the active ingredient is obtained in this manner.

VII. 30 parts by weight of active ingredient No. 15 are thoroughly mixed with a mixture of 92 parts by weight of silica gel powder and 8 parts by weight of liquid paraffin, which was sprayed onto the surface of the silica gel. A formulation of the active ingredient having good adhesion is obtained in this manner.

VIII. 20 parts by weight of active ingredient No. 18 are thoroughly mixed with 2 parts by weight of the calcium salt of dodecylbenzenesulfonic acid, 8 parts by weight of a fatty alcohol polyglycol ether, 2 parts by weight of the sodium salt of a phenol/urea/formaldehyde condensate and 68 parts by weight of a paraffinic mineral oil. A stable oily dispersion is obtained.

The herbicides or the active ingredients can be applied by the preemergence or postemergence method. If the active ingredients are not very well tolerated by certain crops, it is possible to use application methods in which the herbicides are sprayed with the aid of sprays in such a way that the leaves of the sensitive crops are as far as possible not affected while the active ingredients reach the leaves of undesirable plants growing underneath or the uncovered soil surface (post-directed, lay-by).

The application rates of active ingredient are from 0.001 to 3, preferably from 0.01 to 1, kg/ha of active substance (a.s.), depending on the aim of control, the season, the target plants and the stage of growth.

The compounds I can also be used for the desiccation of cotton since they promote the formation of separating tissue between the leaf and the shoot. Also, the shortened maturing time of the cotton plants leads to an increase in quality of the harvested fibers.

In view of the versatility of the application methods, the novel compounds or agents containing them can also be used in a number of further crops for eliminating undesirable plants. Examples of suitable crops are the following:

| Botanical name | Common name |
| --- | --- |
| *Allium cepa* | onions |
| *Ananas comosus* | pineapples |
| *Arachis hypogaea* | peanuts (groundnuts) |
| *Asparagus officinalis* | asparagus |
| *Beta vulgaris* spp. *altissima* | sugarbeets |
| *Beta vulgaris* spp. *rapa* | fodder beets |
| *Brassica napus* var. *napus* | rapeseed |
| *Brassica napus* var. *napobrassica* | swedes |
| *Camellia sinensis* | tea plants |
| *Carthamus tinctorius* | safflower |
| *Carya illinoinensis* | pecan trees |
| *Citrus limon* | lemons |
| *Citrus sinensis* | orange trees |
| *Coffea arabica* (*Coffea canephora*, *Coffea liberica*) | coffee plants |
| *Cucumis sativus* | cucumbers |
| *Cynodon dactylon* | Bermudagrass in turf and lawns |
| *Daucus carota* | carrots |
| *Elaeis guineensis* | oil palms |
| *Fragaria vesca* | strawberries |
| *Glycine max* | soybeans |
| *Gossypium hirsutum* (*Gossypium arboreum* *Gossypium herbaceum* *Gossypium vitifolium*) | cotton |
| *Helianthus annuus* | sunflowers |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |
| *Medicago sativa* | alfalfa (lucerne) |
| *Musa* spp. | banana plants |
| *Nicotiana tabacum* (*N. rustica*) | tobacco |
| *Olea europaea* | olive trees |
| *Oryza sativa* | rice |
| *Phaseolus lunatus* | limabeans |
| *Phaseolus vulgaris* | snapbeans, green beans, dry beans |
| *Picea abies* | Norway spruce |
| *Pinus* spp. | pine trees |
| *Pisum sativum* | English peas |
| *Prunus avium* | cherry trees |
| *Prunus persica* | peach trees |
| *Pyrus communis* | pear trees |
| *Ribes sylvestre* | redcurrants |
| *Ricinus communis* | castor-oil plants |
| *Saccharum officinarum* | sugar cane |
| *Secale cereale* | rye |
| *Solanum tuberosum* | Irish potatoes |
| *Sorghum bicolor* (*s. vulgare*) | sorghum |
| *Theobroma cacao* | cacao plants |
| *Trifolium pratense* | red clover |
| *Triticum aestivum* | wheat |
| *Triticum durum* | durum wheat |
| *Vicia faba* | tick beans |
| *Vitis vinifera* | grapes |
| *Zea mays* | Indian corn, sweet corn, maize |

To extend the action spectrum and to achieve synergistic effects, the styrene derivatives I can be mixed with a large number of members of other groups of herbicidal or growth-regulating active ingredients and applied together with them. Examples of suitable components for the mixture are diazines, 4H-3,1-benzoxazine derivatives, benzothiadiazinones, 2,6-dinitroanilines, N-phenylcarbamates, thiocarbamates, halocarboxylic acids, triazines, amides, ureas, diphenyl ethers, triazinones, uracils, benzofuran derivatives, cyclohexane-1,3-dione derivatives, quinolinecarboxylic acid derivatives, sulfonylureas, aryloxy-and hetaryloxyphenoxypropionic acids and their salts, esters and amides and others.

It may also be advantageous to apply the novel compounds I, alone or in combination with other herbicides, also as a mixture with other crop protection agents, for example with pesticides or agents for controlling phytopathogenic fungi or bacteria. The miscibility with mineral salt solutions which are used for eliminating nutrient and trace element deficiencies is also of interest. Nonphytotoxic oils and oil concentrates may also be added.

PREPARATION EXAMPLES

EXAMPLE 1

N-(3-(2-Chlorobut-1-en-3-onyl)-4-chlorophenyl)-dimethylmaleimide (Compound No. 01)

70 ml of a solution of 12.3 g (35 mmol) of acetyl(chloro)methylenetriphenylphosphorane in ethanol were initially taken at room temperature and 2.1 g (8 mmol) of N-(4-chloro-3-formylphenyl)-dimethylmaleimide were added. The mixture was stirred for 4 hours at about 20° to 25° C. temperature, after which it was cooled to −10° C. and the solid was separated off, washed with a little cold ethanol and was dried at 40° C. under reduced pressure. Yield 89%; top.: 173°–179° C.

EXAMPLE 2

N-(5-(2-Chlorobut-1-en-3-onyl)-4-chloro-2-fluorophenyl)-4,5,6,7-tetrahydrophthalimide (Compound No. 02)

12.3 g (35 mmol) of acetyl (chloro)methylenetriphenylphosphorane in 70 ml of ethanol were initially taken and 2.15 g (7 mmol) of N-(4-chloro-2-fluoro-5-formylphenyl)-4,5,6,7-tetrahydrophthalimide were added. Stirring was carried out for 1 hour at about 20° C., the mixture was cooled to −10° C. and filtered under suction and the residue was washed with a little cold ethanol. Further solid could be isolated from the mother liquor by concentrating it by evaporation. The crude product was dried at 40° C. under reduced pressure. Yield 67%; mp.: 141°–142.5° C.

EXAMPLE 3

N-(5-(2-Chlorobut-1-en-3-onyl)-2,4-difluorophenyl)-4,5,6,7-tetrahydrophthalimide (Compound No. 03)

12.3 g (35 mmol) of acetyl(chloro)methylenetriphenylphosphorane in 70 ml of ethanol were initially taken and 2.3 g (8 mmol) of N-(2,4-difluoro-5-formylphenyl)-4,5,6,7-tetrahydrophthalimide were added. Stirring was carried out for 1 hour at 20°-25° C., the mixture was cooled to −10° C. and filtered under suction and the residue was washed with a little cold ethanol and dried at 35° C. under reduced pressure. Yield 82%; mp.: 170°–172° C.

EXAMPLE 4

N-(5-(2-Chloro-2-cyanoethenyl)-2,4-difluorophenyl)-4,5,6,7-tetrahydrophthalimide (Compound No. 04)

8.7 g (26 mmol) of chloro(cyano)methylenetriphenylphosphorane in 20 ml of ethanol were initially taken and 2.3 g (8 mmol) of N-(2,4-difluoro-5-formylphenyl)-4,5,6,7-tetrahydrophthalimide were added. Stirring was carried out for 3 hours at about 20°–25° C., the mixture was cooled to −10° C. and filtered under suction and the residue was washed with a little cold methanol. Further solid could be isolated from the mother liquor by concentrating it by evaporation. The solid was dried at 40° C. under reduced pressure. Yield: 40%; top.: 140.5°–142° C.

The styrene derivatives I listed in Table 6 were prepared similarly to Examples 2–4 with the appropriate starting compounds.

TABLE 6

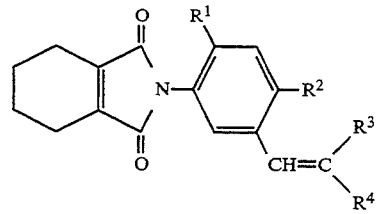

I (A = A₂; n = 0)

| No. | R¹ | R² | R³ | R⁴ | mp. [°C.] |
|---|---|---|---|---|---|
| 05 | H | Cl | H | CN | 167–169 |
| 06 | H | Cl | CH₃ | CN | 112–113 |
| 07 | H | Cl | CH(CH₃)₂ | CN | 161–162 |
| 08 | H | Cl | Cl | CN | oil |
| 09 | H | Cl | Br | CN | oil |
| 10 | F | Cl | H | CN | oil |
| 11 | F | Cl | Cl | CN | |
| 12 | H | Cl | Cl | CO—CH₃ | oil |
| 13 | H | Cl | Br | CO—CH₃ | 126, 5–128 |
| 14 | H | Cl | Br | CO—C₂H₅ | 116–118 |

EXAMPLE 5

N-(3-(2-Chloro-2-cyanoethenyl)-4-chlorophenyl)-dimethylmaleimide (Compound No. 15)

A mixture of 8.4 g (25 mmol) of chloro(cyano)methylenetriphenylphosphorane in 40 ml of methanol was initially taken and 2.6 g (10 mmol) of N-(4-chloro-3-formylphenyl)-dimethylmalemide were added. Stirring was carried out for 4 hours at about 20°–25° C., the mixture was cooled to −10° C. and the solid was separated off, washed with a little cold methanol and dried at 30° C. under reduced pressure. Yield 69%; mp.: 139°–140.5° C.

The compounds in Table 7 were prepared similarly to Example 5.

TABLE 7

I (R¹, R³ = H; R² = Cl)

| No. | A | R⁴ | mp. [°C.] |
|---|---|---|---|
| 16. | (Cl-cyclohexene-pyrazole) | CN | 101–103 |
| 17. | (piperidine-thiadiazine-S,S-dioxide) | CN | 200–202 |
| 18. | (piperidine-thiadiazine-S,S-dioxide) | CO—CH₃ | 95–99 |

USE EXAMPLES

The herbicidal action of the styrene derivatives I was demonstrated by means of greenhouse experiments: The culture vessels used were plastic flower pots containing loamy sand with about 3.0% of humus as a substrate. The seeds of the test plants were sown separately according to species.

In the preemergence treatment, the active ingredients suspended or emulsified in water were applied directly after sowing, by means of finely distributing nozzles. The vessels were lightly watered in order to promote germination and growth and then covered with transparent plastic covers until the plants had started to grow. This covering ensures uniform germination of the test plants, unless this has been adversely affected by the active ingredients. according to the species. The test period extended over from 2 to 4 weeks. During this time, the plants were tended and their reaction to the individual treatments was evaluated.

Evaluation was based on a scale from 0 to 100. 100 means no emergence of the plants or complete destruction of at least the above-ground parts and 0 means no damage or normal growth.

The plants used in the greenhouse experiments consisted of the following species:

| Botanical name | Common name |
|---|---|
| Abutilon theophrasti | velvetleaf |
| Amaranthus retroflexus | redroot pigweed |
| Oryza sativa | rice |
| Solanum nigrum | black nightshade |
| Ipomoea subspecies | morning-glory and related species |
| Triticum aestivum | spring wheat |

Using 0.03 and 0.015 kg/ha of active substance in the postemergence method, undesirable broad-leaved plants can be very well controlled with Example 2. Compound 2 is also tolerated by the crops spring wheat and rice.

For the postemergence treatment, the test plants were first allowed to reach a height of growth of from 3 to 15 cm, depending on the form of growth, before being treated with the active ingredients suspended or emulsified with water. The application rate for the postemergence treatment was 0.03 kg/ha of active substance.

The plants were kept at 10°–25° C. or 20°–35° C.

We claim:

1. A styrene derivative of the formula I $$\begin{array}{c} R^1 \\ A - \text{C}_6H_3 - R^2 \\ \text{CH}=\text{R}^3 \\ R^4 \end{array}$$ I where $R^1$ is hydrogen or halogen, $R^2$ is halogen, $R^3$ is hydrogen, halogen or $C_1$–$C_4$-alkyl, $R^4$ is cyano or $C_1$–$C_6$-alkylcarbonyl and A is a heterocyclic radical selected from the groups $A_1$ to $A_5$

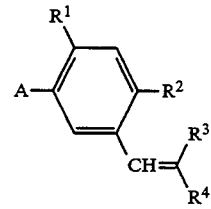

A₁

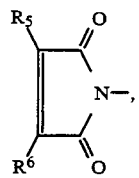

A₂

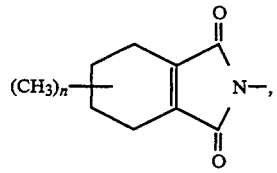

A₃

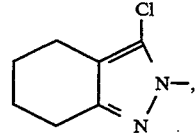

A₄

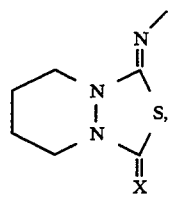

-continued

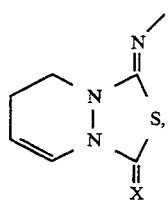   A5 where $R^5$ and $R^6$ are each hydrogen, methyl or ethyl, n is 0 or 1 and X is oxygen or sulfur, with the proviso that n is 0, $R^1$ is hydrogen or fluorine, $R^2$ is chlorine, $R^3$ is chlorine, and $R^4$ is methylcarbonyl when A is the radical $A_2$ or agriculturally useful salts thereof.

2. A method for the defoliation of cotton, wherein the cotton plants are treated with an effective amount of a styrene derivative of the formula I

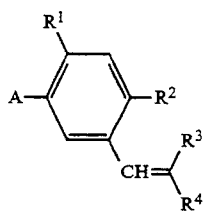   I where $R^1$ is hydrogen or halogen, $R^2$ is halogen, $R^3$ is hydrogen, halogen or $C_1$-$C_4$-alkyl, $R^4$ is cyano or $C_1$-$C_6$-alkylcarbonyl and A is a heterocyclic radical selected from the groups $A_1$ to $A_5$

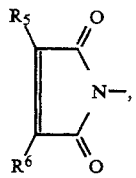   $A_1$

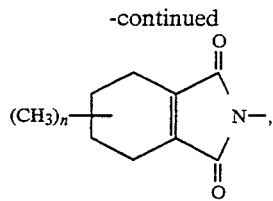   $A_2$

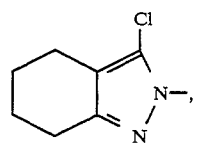   $A_3$

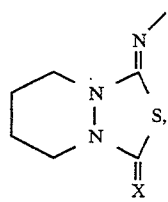   $A_4$

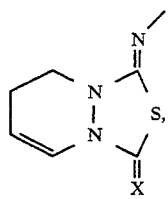   $A_5$ where $R^5$ and $R^6$ are each hydrogen, methyl or ethyl, n is 0 or 1 and X is oxygen or sulfur, with the proviso that $R^4$ is $C_1$-$C_6$-alkylcarbonyl when $R^1$ is hydrogen and at the same time A is the radical $A_2$ where n is 0, or agriculturally useful salts thereof.

3. A herbicide containing conventional inert additives and at least one styrene derivative of the formula I as claimed in claim 1.

4. A method for controlling undesirable plant growth, wherein the undesirable plants or their habitat are or is treated with a herbicidal amount of a styrene derivative of the formula I as claimed in claim 1.

* * * * *